United States Patent [19]

Müller et al.

[11] Patent Number: 5,264,485
[45] Date of Patent: Nov. 23, 1993

[54] HYDROXYALKYL (METH)ACRYLIC-CONTAINING ADHESIVE COMPONENT FOR THE RESTORATION OF DENTAL HARD SUBSTANCE

[75] Inventors: Michael Müller, Bergisch Gladbach; Wolfgang Podszun, Cologne; Werner Finger, Neuss, all of Fed. Rep. of Germany

[73] Assignee: Bayer Aktiengesellschaft, Leverkusen, Fed. Rep. of Germany

[21] Appl. No.: 939,184

[22] Filed: Sep. 2, 1992

[30] Foreign Application Priority Data

Sep. 9, 1991 [DE] Fed. Rep. of Germany ....... 4129877

[51] Int. Cl.$^5$ .......................... C08J 5/24; C08K 5/16; C08L 33/12
[52] U.S. Cl. .................................. 524/724; 524/224; 524/308; 524/309; 523/115; 523/116
[58] Field of Search ............... 524/224, 308, 309, 724; 523/115, 116

[56] References Cited

U.S. PATENT DOCUMENTS

| | | | |
|---|---|---|---|
| 4,937,144 | 6/1990 | Podszun et al. | 428/402 |
| 5,132,335 | 7/1992 | Muller et al. | 522/96 |
| 5,147,903 | 9/1992 | Podszun et al. | 523/115 |

OTHER PUBLICATIONS

Robert S. Baratz, D.D.S., Ph.D., *Present Uses of Polymers in Dentistry—An Introduction*, 1987, pp. 316-326.
E. C. Munksgaard, "Bond Strength Between Dentin and Restorative Resins Mediated by Mixtures of HEMA and Glutaraldehyde," in *Materials Science*, 1985, pp. 1087-1089.
E. Asmussen, "Adhesion of restorative resins to dentinal tissues," 1985, pp. 217-241.
Derwent Publications Ltd., AN 81-50842D.

*Primary Examiner*—Paul R. Michl
*Assistant Examiner*—U. K. Rajguru
*Attorney, Agent, or Firm*—Sprung Horn Kramer & Woods

[57] ABSTRACT

The invention relates to formulations for use as an adhesive component in the restoration of dental hard substance.

6 Claims, No Drawings

HYDROXYALKYL (METH)ACRYLIC-CONTAINING ADHESIVE COMPONENT FOR THE RESTORATION OF DENTAL HARD SUBSTANCE

The invention relates to formulations for use as an adhesive component in the restoration of dental hard substance.

A particularly serious problem in preservative dentistry is the permanent joining, without gaps at the edges, of filling materials of plastic to the dental hard substance (dentine and enamel). Polymeric materials which cure are used as filling materials for tooth repairs in the dental sector. Acrylate-based fillings are in general preferred as curing polymeric materials, but these shrink during curing and in this way contribute to the formation of gaps at the edges.

These polymeric fillings furthermore have the disadvantage that they adhere poorly to the dentine. To solve this problem, the dentine has hitherto been partly undercut; for this, it was necessary to remove considerable amounts of fresh dentine beyond the region attacked. In another method, the dentine and the enamel surface is etched superficially with acids, such as, for example, phosphoric acid, and the filling is then made.

Adhesive formulations, binding of which to the curing acrylate filling is achieved by copolymerisation with the adhesive constituent of the formulation, have been described to improve the adhesion between the dental hard substance and filling material of plastic. These adhesives therefore all contain acrylate groups. Attempts have often been made to employ the readily accessible, inexpensive and readily tolerated 2-hydroxyethyl methacrylate (HEMA) as the adhesive constituent. However, it was found that HEMA could not be formulated by itself to give an effective dental adhesive, but that a specific additive always had to be added.

Munksgaard and Asmussen describe aqueous mixtures of HEMA and glutarodialdehyde as the additive (J. Dent. Res. 63 (1984) 1087).

As the amount of glutarodialdehyde decreases, the adhesive action decreases significantly, and is no longer present if the aldehyde is omitted. The lack of cell tolerance, for example on human gingiva fibroblasts, of this product caused by the aldehyde is criticised in the literature (A. Brauner, W. Krüger, P. Kaden, F. Lampert, C. Mittermayer, Dtsch. Zahnärztl. Z. 43 (1988) 396).

The commercially available adhesive formulations from Kuraray (Clearfil Photobond, Clearfil New Bond, Clearfil Binding Agent) contain, in addition to HEMA, additives of the type of methacrylates containing dihydrogenphosphate or hydrogenphosphate groups. In the end, these additives cause the adhesive action (E. Asmussen, E. C. Munksgaard, in "Posterior Composite Resin Dental Restorative Materials", Peter Szulc Publishing Co. 1985, page 217). The specific methacrylates of this type can be prepared only by expensive syntheses.

A formulation has now been found for use as the adhesive component for the dental hard substance, comprising A) 10 to 90% by weight of hydroxyalkyl (meth)acrylate of the formula $$H_2C=CR^1-CO-O-R^2-OH \qquad (I)$$

in which $R^1$ represents hydrogen or methyl and
$R^2$ represents a divalent alkyl radical having 2 to 6 C atoms, B) 1 to 50% by weight of N-hydroxyalkylcarboxamide of the formula $$R^3-CO-NR^4-R^5-OH \qquad (II)$$

in which $R^3$ represents hydrogen or a monovalent alkyl radical having 1 to 3 C atoms,
$R^4$ represents hydrogen or methyl and
$R^5$ represents a divalent hydrocarbon radical having 2 to 6 C atoms, and if appropriate C) 0.01 to 2.0% by weight of initiators and/or 0.01 to 4.0% by weight of coactivators and/or
D) 5 to 90% by weight of solvent and/or
E) 0.3 to 80% by weight of (meth)acrylic acid esters which can form crosslinkings, the sum of all the constituents being 100% by weight.

(Meth)acrylic acid derivatives in the context of this invention are derivatives of methacrylic acid or acrylic acid.

Divalent alkyl radicals $R^2$ are straight-chain or branched-chain aliphatic alkyl radicals having 2 to 6 C atoms. Suitable hydroxyalkyl (meth)acrylates A are accordingly, for example, 4-hydroxybutyl methacrylate, 4-hydroxybutyl acrylate and 3-hydroxypropyl methacrylate. 2-hydroxypropyl methacrylate and 2-hydroxyethyl acrylate may be mentioned as preferred. 2-hydroxyethyl methacrylate is particularly preferred.

The formulations according to the invention in general contain 10 to 90% by weight of hydroxyalkyl (meth)acrylates, preferably 15 to 60% by weight and particularly preferably 20 to 40% by weight.

In the N-hydroxyalkylcarboxamides B according to formula (II), $R^3$ represents hydrogen, methyl, ethyl, propyl or isopropyl, $R^4$ represents hydrogen or methyl and $R^5$ represents a divalent aliphatic, aromatic, straight-chain or branched-chain hydrocarbon radical having 2 to 6 C atoms. Suitable N-hydroxyalkylcarboxamides which may be mentioned are N-2-hydroxyethylacetamide
N-2-hydroxypropylacetamide
N-3-hydroxypropylformamide
N-2-hydroxyethylbutyric acid amide
N-2-hydroxypropyl-N-methylacetamide
N-2-hydroxyethyl-N-methylformamide
$H_3C-CO-NH-CH_2-CH_2-OH$,
$H_3C-CO-NH-CH_2-CHCH_3-OH$,
$H-CO-NH-CH_2-CH_2-CH_2-OH$,
$H_7C_3-CO-NH-CH_2-CH_2-OH$,
$H_3C-CO-NCH_3-CH_2-CHCH_3-OH$
and
$H-CO-NCH_3-CH_2-CH_2-OH$.

Preferred compounds are

N-p-hydroxyphenylformamide
N-p-hydroxyphenylacetamide
N-2-hydroxyethylpropionamide
N-5-hydroxypentylformamide

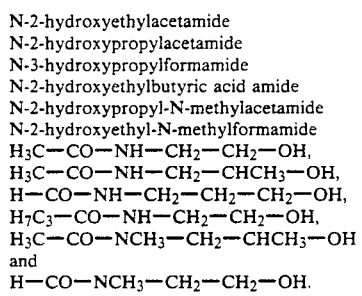

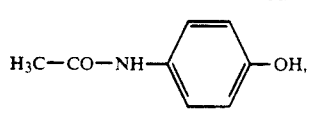

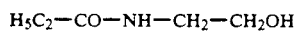

and

H—CO—NH—(CH₂)₅—OH.

Particularly preferred N-hydroxyalkylcarboxamides B are

N-5-hydroxypentylacetamide
N-2-hydroxypropylpropionamide
N-2-hydroxyethyl-N-methylpropionamide
N-3-hydroxypropyl-N-methylacetamide
N-3-hydroxypropylacetamide
N-3-hydroxypropylpropionamide
N-3-hydroxypropylbutyric acid amide
H₃C—CO—NH—(CH₂)₅—OH,
H₅C₂—CO—NH—CH₂—CHCH₃—OH,
H₅C₂—CO—NCH₃—CH₂—CH₂—OH,
H₃C—CO—NCH₃—CH₂—CH₂—CH₂—OH,
H₃C—CO—NH—CH₂—CH₂—CH₂—OH,
H₅C₂—CO—NH—CH₂—CH₂—CH₂—OH
and
H₇C₃—CO—NH—CH₂—CH₂—CH₂—OH.

The formulations according to the invention in general contain 1 to 50% by weight of N-hydroxyalkylcarboxamides, preferably 5 to 30 and particularly preferably 10 to 20% by weight.

N-Hydroxyalkylcarboxamides are compounds which are known per se and can be prepared, for example, by acylation of hydroxyalkylamines with carboxylic acid esters, in particular carboxylic acid methyl or carboxylic acid ethyl esters, in an organic solvent, such as, for example, methanol or ethanol, or else without a solvent at between 60° and 100° C. Hydroxyalkylformamides can in principle also be obtained by carbonylation of aminoalcohols with carbon monoxide under pressure (U.S. Pat. No. 2,793,211). N-p-hydroxyphenylformamide can furthermore be synthesised from p-aminophenol and formic acid in water (Beilsteins Handbuch der Organischen Chemie (Beilsteins' Handbook of Organic Chemistry), 4th Edition, Volume 13, 1930, page 459).

The solvents in the context of the present invention should dissolve the components and should not be toxic, because of the application. Water and volatile organic solvents, such as methanol, ethanol, propanol, isopropanol, acetone, methyl ethyl ketone, methyl or ethyl acetate or tetrahydrofuran, may be mentioned as preferred. In general, 5 to 90% by weight, preferably 20 to 80% by weight and particularly preferably 40 to 75% by weight, of the solvent is employed.

Initiators in the context of the present invention are agents which form free radicals and which trigger off free radical polymerisation. Photoinitiators which trigger off free radical polymerisation under the action of light, for example UV light, visible light or laser light, are preferred.

The so-called photopolymerisation initiators are known per se (Houben-Weyl, Methoden der organischen Chemie (Methods of Organic Chemistry), Volume E20, page 80 et seq., Georg Thieme Verlag Stuttgart 1987). They are preferably mono- or dicarbonyl compounds, such as benzoin and derivatives thereof, in particular benzoin methyl ether, benzil and benzil derivatives, for example 4,4-oxydibenzil, and other dicarbonyl compounds, such as diacetyl, 2,3-pentanedione and α-diketo derivatives of norbornane and substituted norbornanes, metal carbonyls, such as pentacarbonylmanganese, or quinones, such as 9,10-phenanthrenequinone and naphthoquinone. Camphorquinone is particularly preferred.

The formulations according to the invention in general contain 0 to 2 parts by weight, preferably 0.1 to 0.5 part by weight, of the initiator per part by weight of polymerisable (meth)acrylates A and E contained in the formulations.

If one of the joint components in contact with the adhesive component according to the invention already contains an initiator of the type described, the initiator in the adhesive component can also be dispensed with completely.

It may be advantageous to add coactivators which accelerate the polymerisation reaction to the formulations according to the invention. Examples of known accelerators are amines, such as p-toluidine and dimethyl-p-toluidine, trialkylamines, such as trihexylamine, polyamines, such as N,N,N',N'-tetraalkylalkylenediamines, barbituric acid and dialkylbarbituric acids.

The coactivators are in general employed in an amount of 0 to 4% by weight, preferably 0. 2 to 1% by weight, based on the amount of polymerisable compounds.

It may also be appropriate to add (meth)acrylic acid esters which can form crosslinkings to the compositions according to the invention. (Meth)acrylic acid esters which can form crosslinkings in general contain 2 or more polymerisable active groups in the molecule. Esters of (meth)acrylic acid with di-, tri-, tetra- or pentahydric alcohols having 2 to 30 carbon atoms may be mentioned as preferred. Alkoxy (meth)acrylates and (meth)acrylates containing urethane groups are particularly preferred.

Examples which may be mentioned are (meth)acrylic acid esters of the formula

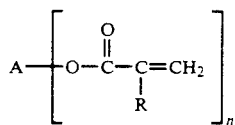

in which
A denotes a straight-chain, branched, cyclic, aliphatic, aromatic or mixed aliphatic-aromatic radical having 2 to 25 C atoms, which can be interrupted by —O— or NH bridges and can be substituted by hydroxyl, oxy, carboxyl, amino or halogen,
R denotes H or methyl and
n represents an integer from 2 to 8, preferably 2 to 4.

Compounds of the following formulae may be mentioned as preferred:

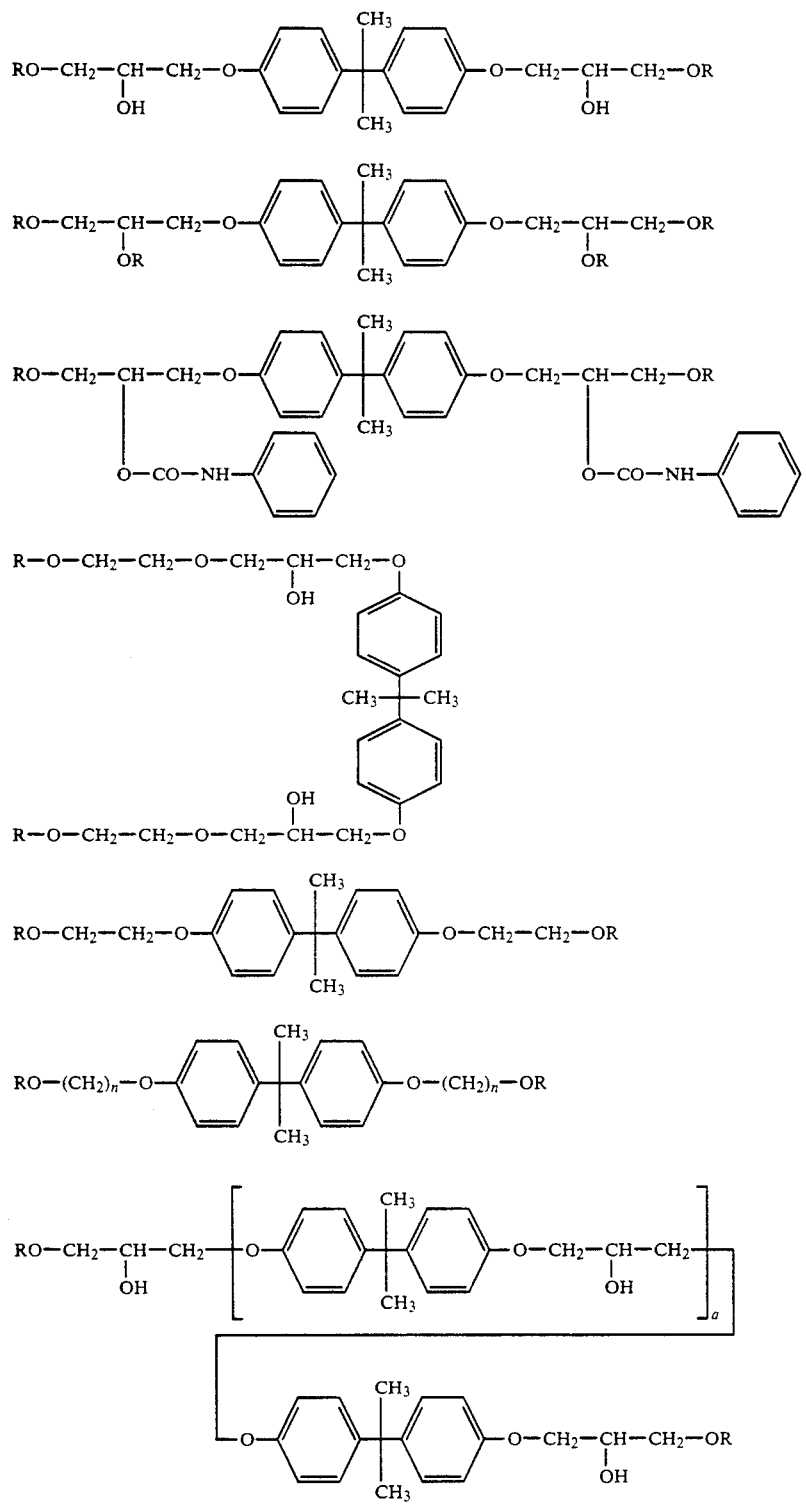
wherein a denotes a number from 1 to 4
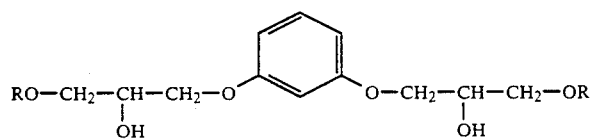

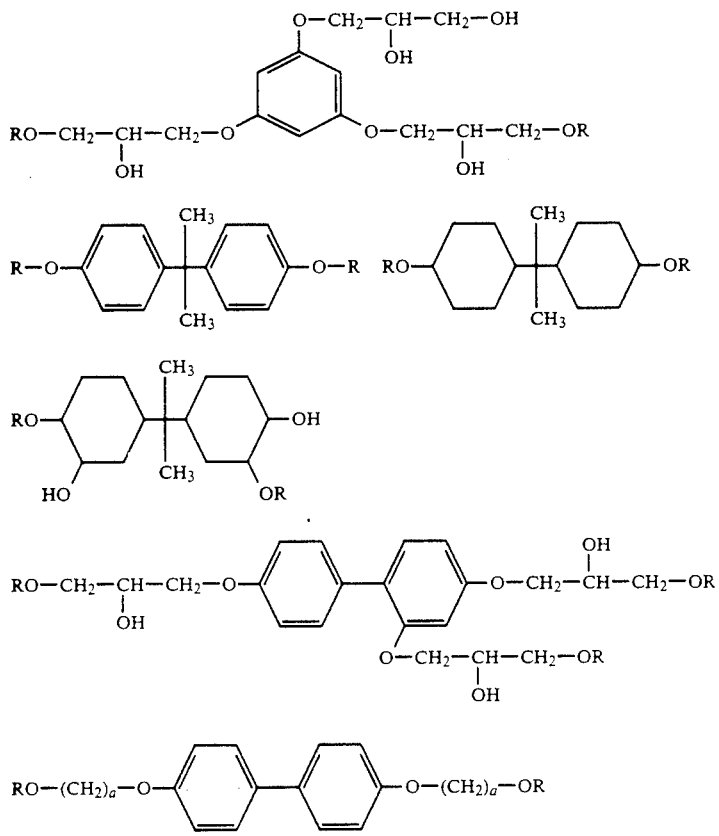
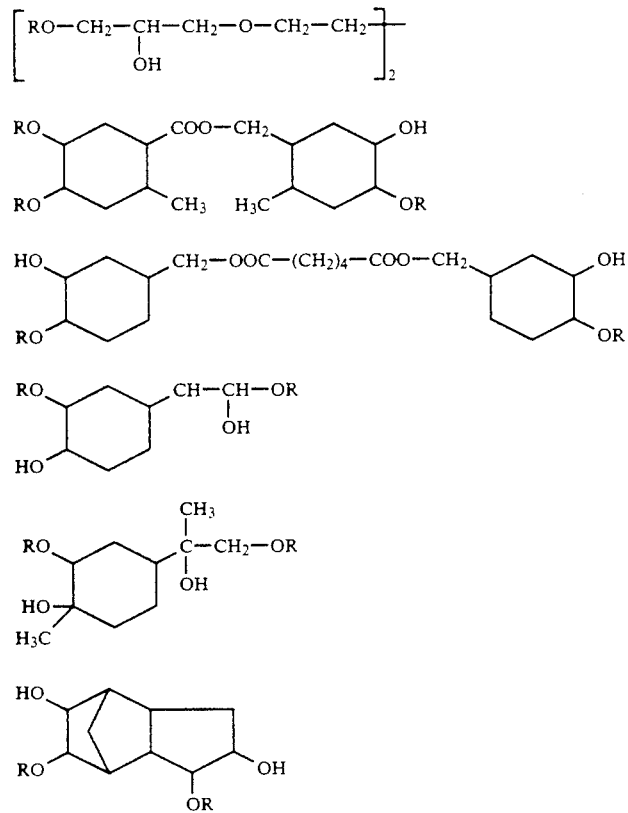
wherein a denotes a number from 1 to 4

-continued
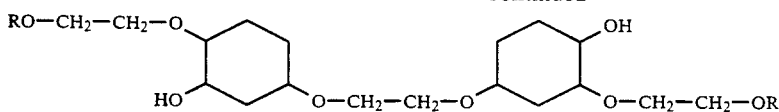
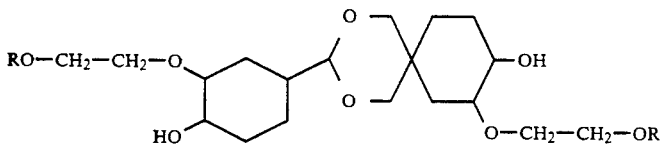
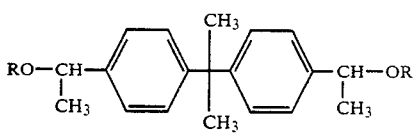
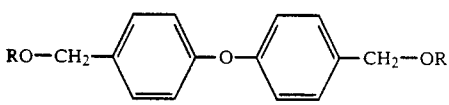
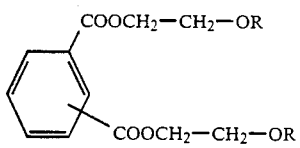
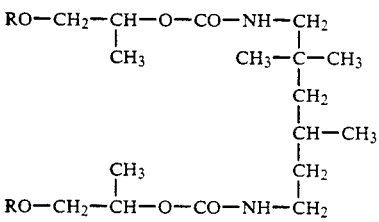
in the ortho-, meta- or para-form
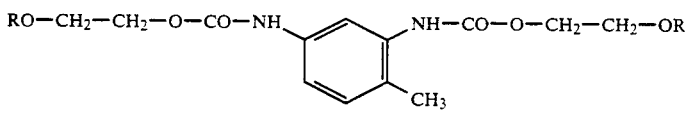
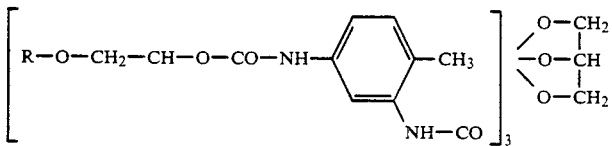
wherein R represents
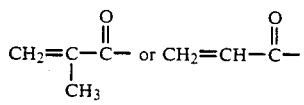

Derivatives of tricylcodecane (EP-A 0 023 686) and reaction products of polyols, diisocyanates and hydroxyalkyl methacrylates (DE-A 37 03 120, DE-A 37 03 080 and DE-A 37 03 130) may also be mentioned. The following monomers may be mentioned as examples:
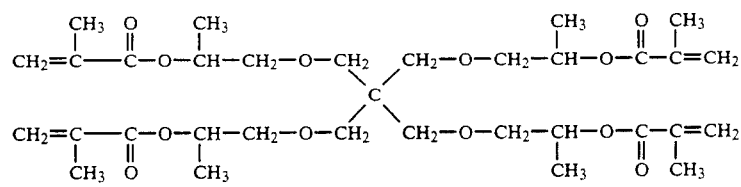
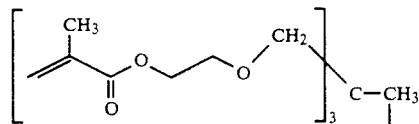
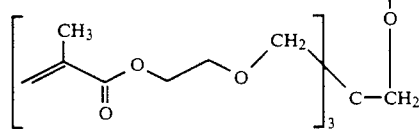
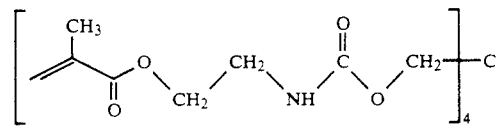
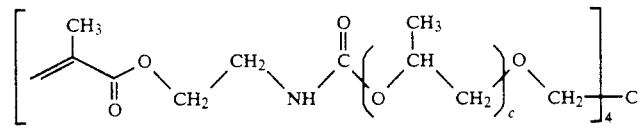
$c = 1.225$ (statistical mean for 4 chains)
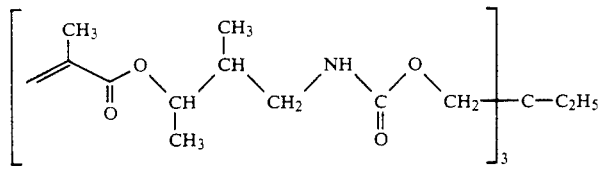
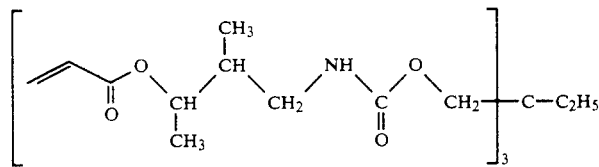
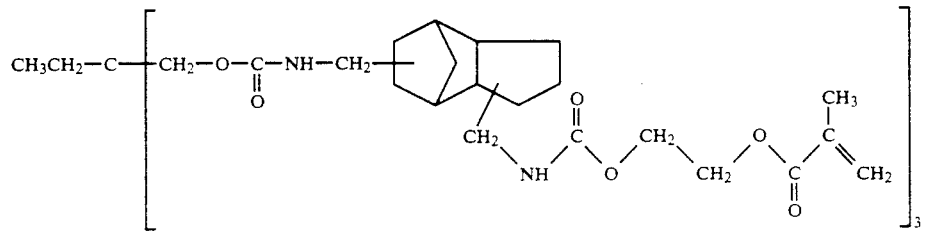

-continued
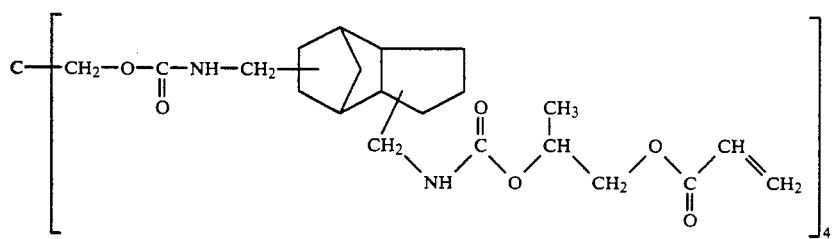
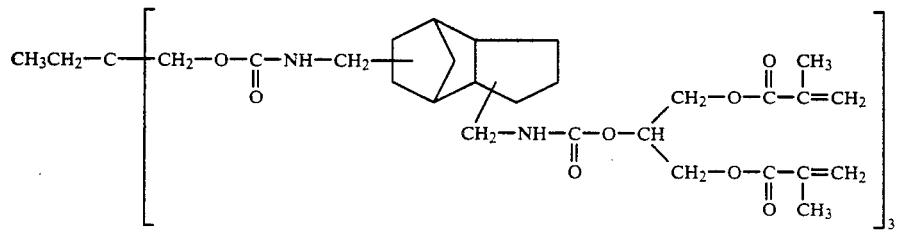
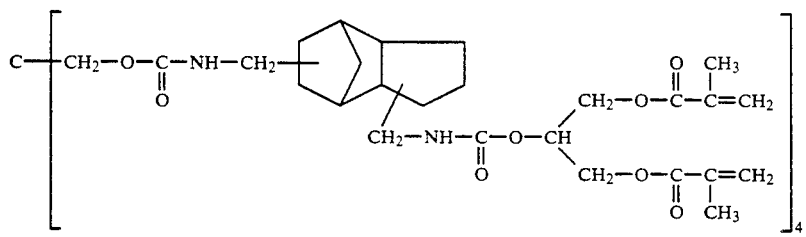
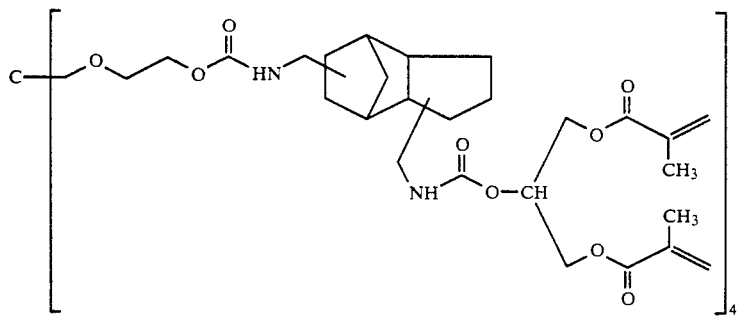
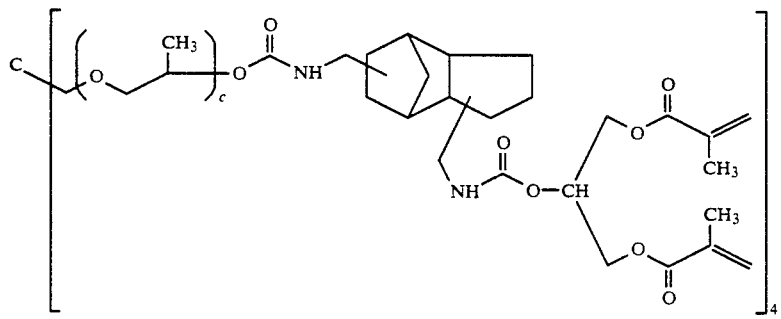
c = 1.225 (statistical mean for 4 chains)

-continued
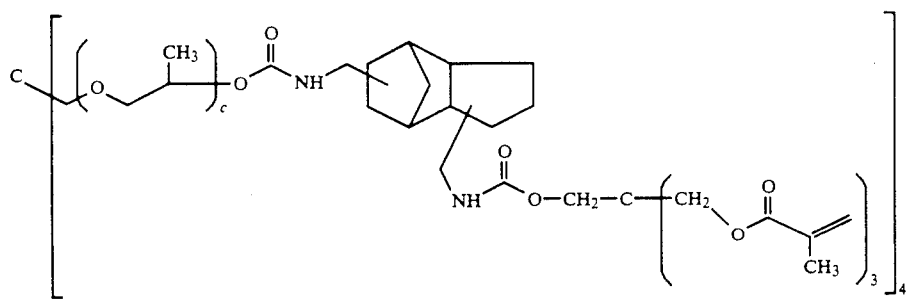
c = 1.225 (statistical mean for 4 chains)
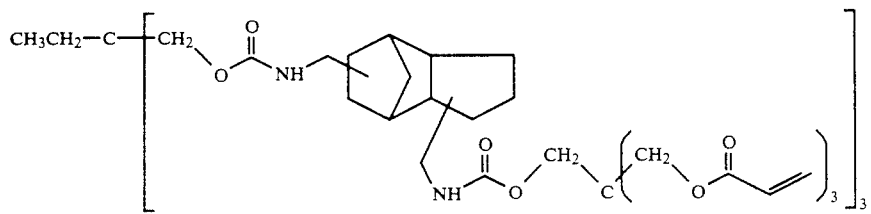
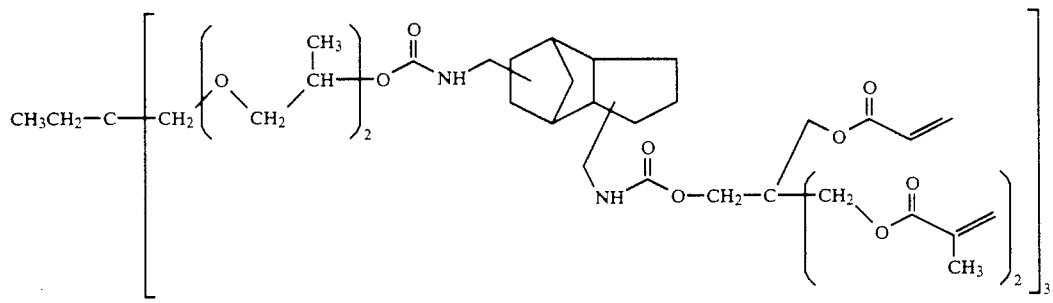
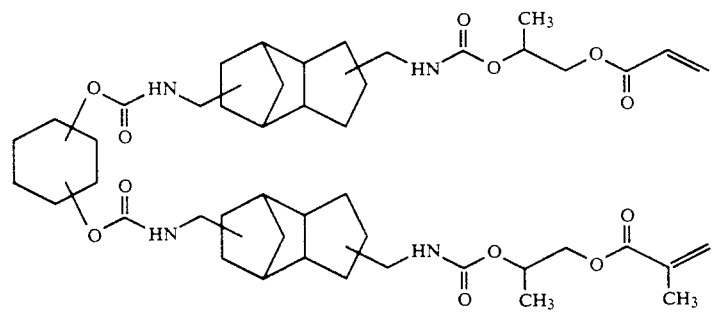
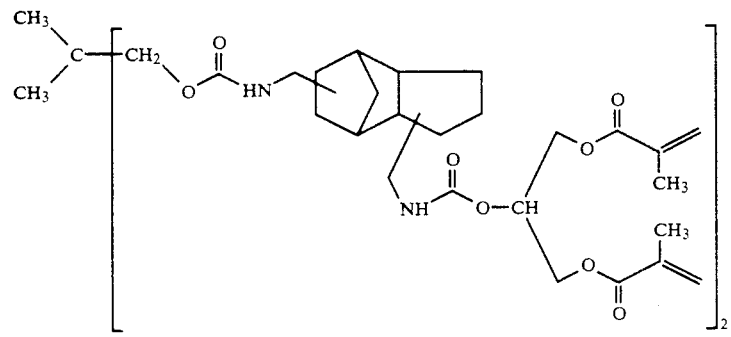

-continued
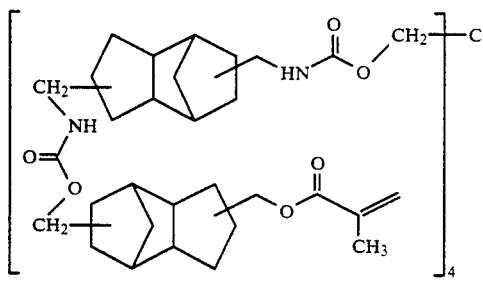
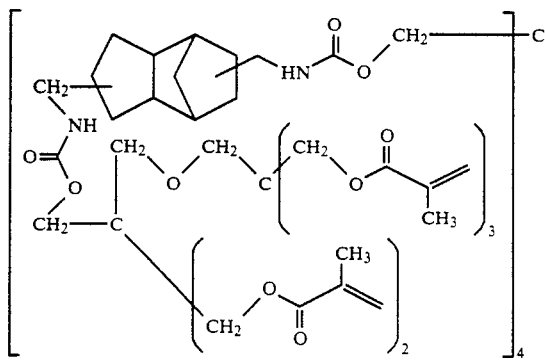
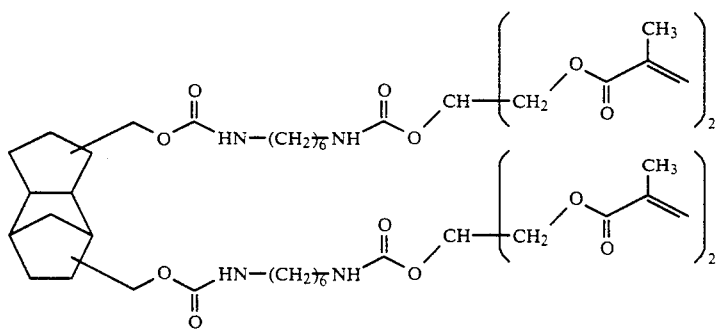
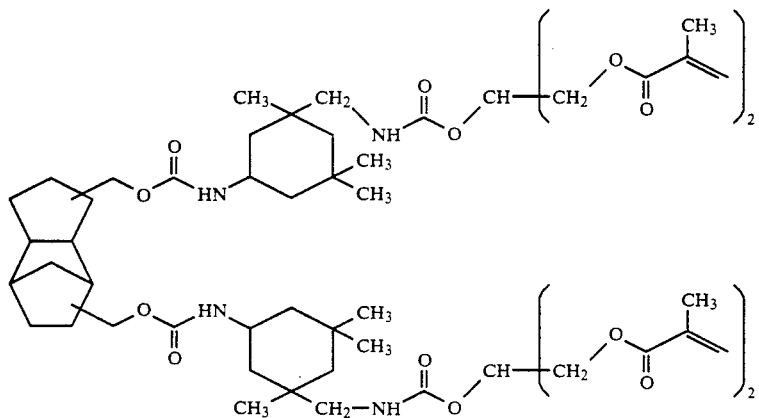

-continued

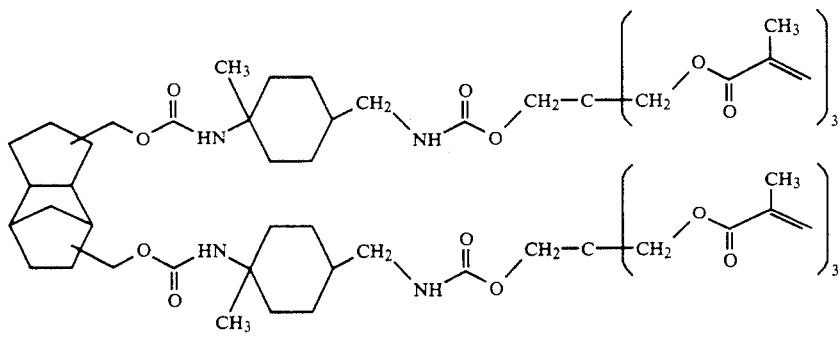

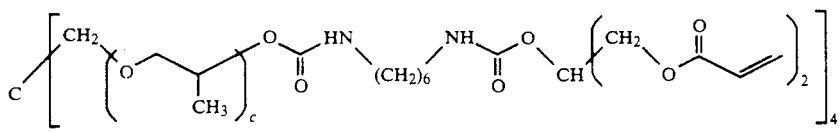

c = 1.225 (statistical mean for 4 chains)

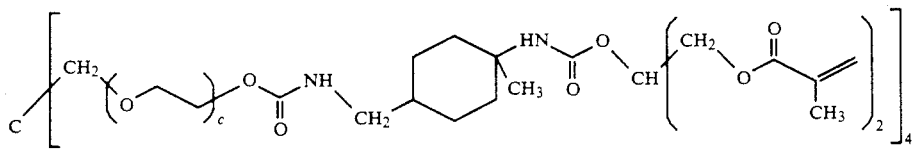

c = 1.225 (statistical mean for 4 chains)

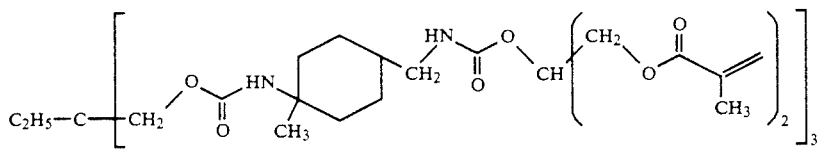

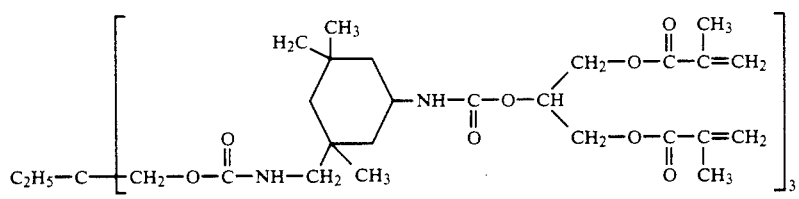

The preferred methacrylic acid ester is so-called bis-GMA of the formula

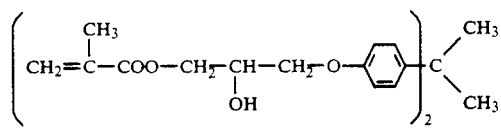

It is of course possible to employ mixtures of the various (meth)acrylic acid esters which can form crosslinkings. Mixtures of 20 to 70 parts by weight of bis-GMA and 30 to 80 parts by weight of triethylene glycol dimethacrylate may be mentioned as examples.

The formulations according to the invention in general contain 0.3 to 80 parts by weight, preferably 1 to 50 parts by weight and particularly preferably 4 to 30 parts by weight of methacrylic acid esters which can form crosslinkings.

The compositions according to the invention can contain fillers as a further component. Fine powders which have a particle diameter in the range from 0.02 to 100 μm (if appropriate also in a polydisperse distribution) are preferred as the fillers. The fillers can be the fillers customary in the dental sector (R. S. Baratz, J. Biomat. Applications, Vol 1, 1987, page 316 et seq.), such as inorganic glasses, silicon dioxide powder, aluminium oxide powder or quartz powder.

Adhesive cements which are particularly suitable for fixing bridges, crowns and other veneer materials are formed by a content of fillers in the formulations according to the invention.

The content of fillers is in general 0 to 80 parts by weight, preferably 15 to 70 parts by weight and particularly preferably 20 to 60 parts by weight, based on the total formulation.

The adhesive components according to this invention can furthermore contain up to 10% by weight of customary additives, such as stabilisers, inhibitors, light stabilisers, dyestuffs, pigments or fluorescent substances.

The formulations according to the invention can be prepared by mixing components A and B or A to E by vigorous stirring.

The formulations according to the invention can be used as the adhesive component for the treatment of dentine and tooth enamel. It must be described as decidedly surprising that the formulations according to the invention allow good adhesion between the dental hard substance and filling material. Asmussen and Munksgaard report that the presence of a reactive aldehyde, such as glutaraldehyde, is necessary to formulate an adhesive with HEMA (J. Dent. Res. 63 (1984) 1087). These authors explain the action of the aldehyde in its reaction with the protein structure of the dentine and subsequent chemical binding of, for example, hydroxyethyl methacrylate to the dentine thus modified (U.S. Pat. No. 4,593,054). However, the formulations according to the present invention contain no components which are capable of reacting with the dental hard substance under the conditions of the oral cavity. In particular, under these conditions the N-hydroxyalkylcarboxamides are completely unreactive towards the dental hard substance and the hydroxyalkyl (meth)acrylate employed. The formulations according to the invention also contain no other components or chemical structural constituents which would be capable, according to the prior art, of allowing binding to the dental hard substance.

The formulations according to the invention allow firm and permanent joining of dental hard substance and filling material on the basis of readily accessible, inexpensive and toxicologically acceptable constituents.

In a particular embodiment, the tooth enamel and dentine are conditioned with a liquid having a pH in the range from 0.1 to 3.5 before the treatment with the formulation according to the invention.

This liquid in general contains acids having a $pK_a$ value of less than 5 and if appropriate an amphoteric amino compound having a $pK_a$ value in the range from 9.0 to 10.6 and a $pK_b$ value in the range from 11.5 to 12.5. The conditioning liquid can contain, for example, the following acids:

phosphoric acid, nitric acid, pyruvic acid, citric acid, oxalic acid, ethylenediaminetetraacetic acid, acetic acid, tartaric acid, malic acid and maleic acid.

Amphoteric amino compounds which may be mentioned are, preferably, compounds of the formula $$\begin{array}{c} H \\ | \\ R^7-C-R^6, \\ | \\ R^8-NH \end{array}$$

in which
$R^6$ represents a carboxyl group,
$R^7$ denotes hydrogen or a lower alkyl radical which is optionally substituted by hydroxyl, thio, methylthio, carboxyl, amino, phenyl, hydroxyphenyl or the groups

[structure: indole group or $H_2N / H_3N$ —C=N— group]

and
$R^8$ denotes hydrogen or phenyl, and wherein the radicals $R^6$ and $R^8$ can be bonded by a propyl radical, or in which
$R^6$ represents hydrogen,
$R^7$ denotes the group

—A—NH$_3$X, in which
A represents a divalent alkylene radical having 1 to 6 carbon atoms and
X represents halogen, and
$R^8$ denotes hydrogen.

The following amphoteric amino compounds may be mentioned as examples: glycine, serine, threonine, cysteine, thysorine, asparagine, glutamine, alanine, valine, leucine, isoleucine, proline, methionine, phenylalanine, tryptophan, lysine, arginine, histidine, N-phenylglycine, ethylenediamine hydrochloride, ethylenediamine hydrobromide, propylenediamine hydrochloride, propylenediamine hydrobromide, butylenediamine hydrochloride, butylenediamine hydrobromide, leucine hydrochloride and histidine hydrochloride.

The conditioning liquid can furthermore contain substances from the group comprising polyethylene glycols and metal hydroxides. In particular, the abovementioned polybasic acids can also be employed as partial metal salts, as long as free acid functions remain.

Conditioning liquids which contain at least one of the acids from the group comprising oxalic acid, ethylenediaminetetraacetic acid and citric acid and if appropriate an amphoteric amino compound from the group comprising glycine, N-phenylglycine and proline are particularly preferred.

The formulations according to the invention can be used, for example, as follows:

During a dental repair, for example, the conditioning liquid is first applied after mechanical preparation of the tooth enamel and dentine and is allowed to act for a short time (for example 60 seconds), and the tooth material is rinsed with water and dried in a stream of air. The formulation according to the invention is then applied in a thin layer, for example with a small brush, and dried in a stream of air. After the treatment according to the invention, the actual filling composition, for example filling compositions of plastic which are customary in the dental sector (K. Eichner, "Zahnärztliche Werkstoffe und ihre Verarbeitung" (Dental Materials and their Processing), Volume 2, page 135 et seq., Hüthig Verlag, 5th Edition 1985), is applied.

The formulations according to the invention can be used in a similar manner for fixing crowns, bridges and similar aids.

EXAMPLES

The adhesive components according to the invention and the comparison component are produced by intensive mixing of the constituents listed in the following examples.

EXAMPLE 1

10.0 g of N-3-hydroxypropylpropionamide 20.0 g of 2-hydroxyethyl methacrylate 70.0 g of water

EXAMPLE 2

10.0 g of N-3-hydroxypropylacetamide 20.0 g of 2-hydroxyethyl methacrylate 70.0 g of water

EXAMPLE 3

10.0 g of N-p-hydroxyphenylformamide 20.0 g of 2-hydroxyethyl methacrylate 70.0 g of water

EXAMPLE 4

10.0 g of N-p-hydroxyethyl-N-methylformamide 20.0 g of 2-hydroxyethyl methacrylate 70.0 g of water

EXAMPLE 5

10.0 g of N-5-hydroxypentylformamide 20.0 g of 2-hydroxyethyl methacrylate 70.0 g of water

EXAMPLE 6 (COMPARISON EXAMPLE)

22 g of 2-hydroxyethyl methacrylate 78 g of water

EXAMPLE 7 (USE TEST, BONDING STRENGTH)

The activity and suitability of the adhesives (Examples 1 to 5) is checked by determination of the shear bonding strength on dentine and enamel. Human teeth which have been kept in 1% chloramine solution for a maximum of three months after extraction are used. Before being used in the test, the teeth are cleaned thoroughly under running water and kept in physiological saline solution for at least three and not more than ten days. On the day before being used in the bonding test, the teeth are embedded individually in cylindrical rubber moulds of 25 mm diameter and 12 mm height using epoxy resin (®LEKUTHERM X20, curing agent T3). The teeth are ground by wet grinding on SiC paper of grain sizes 240, 320, 400 and finally 600 until a sufficiently large enamel surface or a dentine surface close to the enamel for binding to a cylinder of plastic of 3.5 mm diameter is exposed. After rinsing with deionised water and drying in a stream of air, the teeth are cleaned with the conditioning solution and a cotton-wool pellet for 30 seconds, rinsed with water and dried, before the adhesive is applied with a brush, left on the surface for 30 seconds and then dried carefully in a stream of compressed air. The sample pretreated in this way is firmly clamped in a clamping device under a divisible Teflon mould having a cylindrical nest 3.5 mm wide and 1 mm high. The cylindrical mould is then filled with the filling material of plastic ®Pekafill (U) using a syringe, the material is covered with a strip which is impermeable to $O_2$ and is activated with a ®Translux CL (Kulzer) polymerisation lamp under the light discharge opening placed on top for 60 seconds. Immediately thereafter, the sample is removed from the holder. The Teflon mould is removed and the sample is kept in warm water at 23° C. for 15 minutes until the shear stress is initiated, which is effected with the aid of a pressure piston parallel to and close against the surface of the embedded tooth under an advance speed of 1 mm/minute until separation occurs. The shear bonding strength, the quotient of the breaking force and contact area on the tooth, is determined on in each case 3 samples and stated as the mean value thereof.

The results are summarised in the following table:

| Formulation according to Example No. | Shear bonding strength on dentine [N/mm$^2$] |
|---|---|
| 1 | 7.8 |
| 2 | 6.1 |
| 3 | 4.9 |
| 4 | 4.4 |
| 5 | 5.0 |
| 6 (comparison) | <2.0 |

When the cause of fracture was evaluated under a light microscope, cohesive fractures in the dentine or in the plastic were chiefly observed, that is to say the joins produced with the adhesive components according to the invention were stronger than the bonded joint components themselves. This shows the good performance of the adhesive components according to the invention.

We claim:

1. Adhesives for the dental hard substance, comprising
   A) 10 to 90% by weight of hydroxyalkyl (meth)acrylate of the formula

   $$H_2C=CR^1-CO-O-R^2-OH \qquad (I)$$

in which
   R$^1$ represents hydrogen or methyl and
   R$^2$ represents a divalent alkyl radical having 2 to 6 C atoms,
   B) 1 to 50% by weight of N-hydroxyalkylcarboxamide of the formula

   $$R^3-CO-NR^4R^5-OH \qquad (II)$$

in which
   R$^3$ represents hydrogen or a monovalent alkyl radical having 1 to 3 C atoms,
   R$^4$ represents hydrogen or methyl and
   R$^5$ represents a divalent hydrocarbon radical having 2 to 6 C atoms, and if appropriate
   C) 0.01 to 2.0% by weight of initiators and/or 0.01 to 4.0% by weight of coactivators in each case based on the sum of the components from A and E, and/or
   D) 5 to 90% by weight of solvent and/or
   E) 0.3 to 80% by weight of (meth)acrylic acid esters which can form crosslinkings.

2. Adhesives according to claim 1, comprising
   A) 15 to 60% by weight of hydroxyalkyl (meth)acrylate,
   B) 5 to 30% by weight of N-hydroxyalkylcarboxamide,
   C) 0.1 to 5% by weight of initiators and/or 0.2 to 1% by weight of coactivators, in each case based on the sum of the components from A and E, and if appropriate
   D) 20 to 80% by weight of solvent and/or
   E) 1 to 50% by weight of (meth) acrylic acid esters which can form crosslinkings, the amounts data for the components relating to the total formulation, unless stated otherwise.

3. Adhesives according to claim 1, comprising
   A) 20 to 40% by weight of hydroxyalkyl (meth)acrylate,
   B) 0 to 20% by weight of N-hydroxyalkylcarboxamide,
   C) 0.1 to 5% by weight of initiators and/or 0.2 to 1% by weight of coactivators, in each case based on the sum of the components from A and E, and if appropriate
   D) 40 to 75% by weight of solvents and/or E) 4 to 30% by weight of (meth) acrylic acid esters which can form crosslinkings, the amounts data for the components relating to the total formulation, unless stated otherwise.

4. Adhesives according to claim 1, characterised in that N-3-hydroxypropylpropionamide is used as component (B).

5. Adhesives according to claim 1, characterised in that N-3-hydroxypropylacetamide is used as component (B).

6. A method for fixing dental articles to the dental hard substance comprising employing the adhesives according to claim 1.

* * * * *

UNITED STATES PATENT AND TRADEMARK OFFICE
CERTIFICATE OF CORRECTION

PATENT NO. : 5,264,485
DATED : November 23, 1993
INVENTOR(S) : Muller, et al

It is certified that error appears in the above-indentified patent and that said Letters Patent is hereby corrected as shown below:

On the title page: Item [54]

Col. 1, line 2    delete " ACRYLIC " and substitute -- ACRYLATE --

Signed and Sealed this

Twenty-ninth Day of August, 1995

Attest:

BRUCE LEHMAN

Attesting Officer      Commissioner of Patents and Trademarks